United States Patent [19]

Rosenberg née Göldner

[11] Patent Number: 4,919,931
[45] Date of Patent: Apr. 24, 1990

[54] METHOD FOR PRODUCING OSSEIN HYDROXYAPATITE COMPOUND

[75] Inventor: Thea Rosenberg née Göldner, Basel, Switzerland

[73] Assignee: Robapharm AG, Switzerland

[21] Appl. No.: 11,504

[22] Filed: Feb. 5, 1987

[30] Foreign Application Priority Data

Aug. 5, 1986 [DE] Fed. Rep. of Germany ....... 3626414

[51] Int. Cl.⁵ ...................... A61K 35/32; A61K 37/02
[52] U.S. Cl. .................................... 424/95; 514/801; 530/840; 435/70.3; 424/601
[58] Field of Search .................. 424/95, 128; 514/801; 530/840; 435/68

[56] References Cited

U.S. PATENT DOCUMENTS

| | | | |
|---|---|---|---|
| 4,232,425 | 11/1980 | Wojcik | 530/840 |
| 4,294,753 | 10/1981 | Urist | 530/840 |
| 4,427,583 | 1/1984 | England et al. | 530/840 |
| 4,436,720 | 3/1984 | Pakhomov et al. | 424/95 |
| 4,455,256 | 6/1984 | Urist | 530/840 |
| 4,620,327 | 11/1986 | Caplan et al. | 424/95 |

FOREIGN PATENT DOCUMENTS

| | | |
|---|---|---|
| 1302401 | 2/1978 | Fed. Rep. of Germany . |
| 1617317 | 12/1978 | Fed. Rep. of Germany . |
| 2840064 | 10/1982 | Fed. Rep. of Germany . |
| 3409372 | 9/1985 | Fed. Rep. of Germany . |
| 3422466 | 3/1986 | Fed. Rep. of Germany . |

OTHER PUBLICATIONS

Pines et al., Current Medical Research and Opinion, vol. 8, No. 10, (1984), pp. 734–742.
Annefeld et al., cited in Chem. Abstracts, vol. 106589f 1987.
Pines et al., Curr. Med. Res. Opin. 8: pp. 734–742 (1984).
Farley et al., Biochem. 21: pp. 3502–3507 (1982).

Primary Examiner—Jacqueline M. Stone
Attorney, Agent, or Firm—Saidman, Sterne, Kessler & Goldstein

[57] ABSTRACT

A method for producing an ossein hydroxyapatite compound from bones or fetal and young animals is described. The compound so produced stimulates chondrocytes and osteoblasts and is useful in the treatment of osteoarthritis, osteoporosis, bone and cartilage defects, and in the healing of bone fractures.

5 Claims, 14 Drawing Sheets

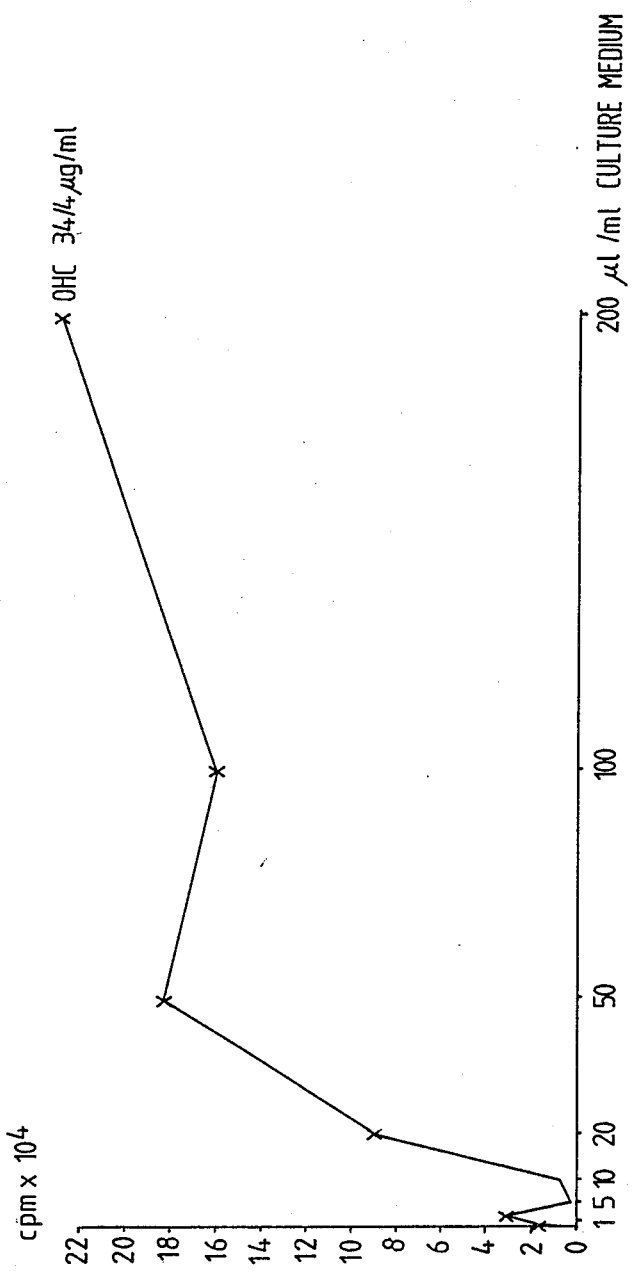

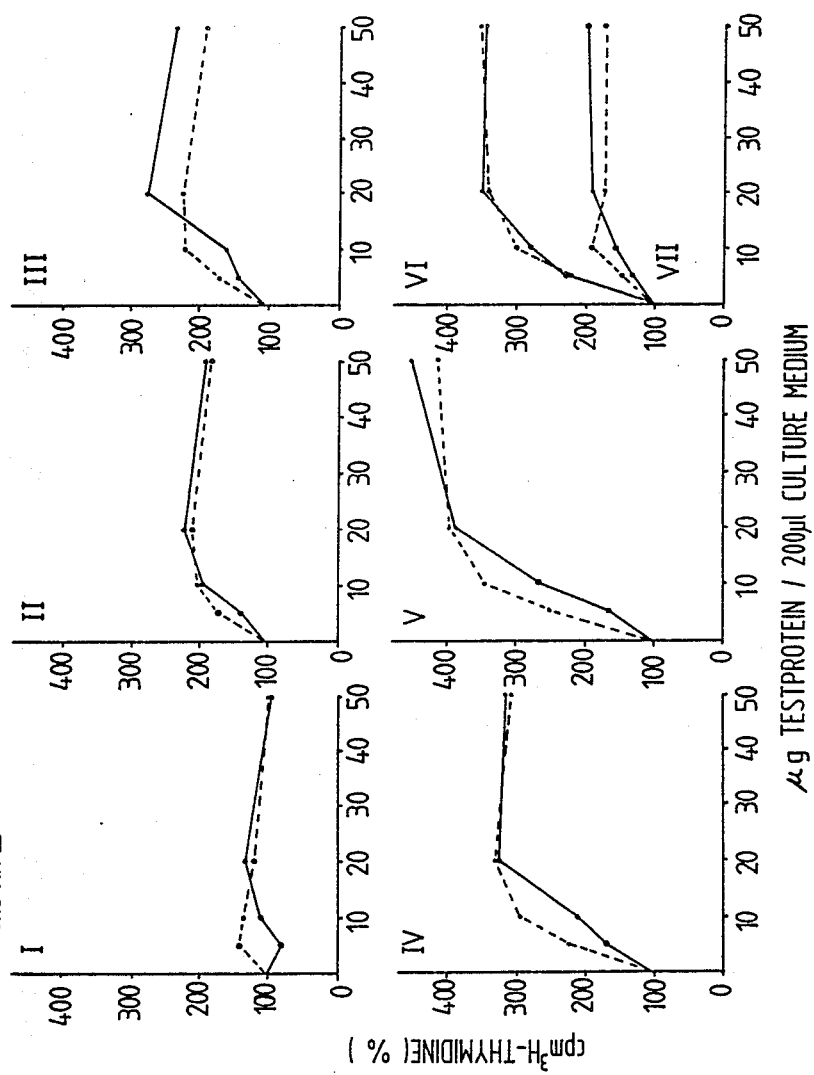

METHOD FOR PRODUCING OSSEIN HYDROXYAPATITE COMPOUND

FIELD OF THE INVENTION

The invention relates to an ossein hydroxyapatite compound (OHC) for the stimulation of chondrocytes and osteoblasts. The invention furthermore relates to methods for producing the OHC. The invention further relates to the use of OHC to manufacture pharmaceutical compositions, especially for oral administration, for the prophylaxis and treatment of osteoarthritis and osteoporosis and for healing bone fractures, cartilage defects and bone defects.

BACKGROUND OF THE INVENTION

A microcrystalline hydroxyapatite composition (MCHC) for the prevention of osteoporosis based on a corticosteroid therapy is already known; see A. Pines et al., Current Medical Research and Opinion, Vol. 8, No. 10, 1984, pp. 734-742. The composition comprises to approximately 50% by wt. a complex salt from hydroxyapatite and calcium phosphate. It further contains about 26% collagen and about 9% non-collagenic proteins/peptides. In addition it contains about 0.65% sodium as well as magnesium and potassium and as trace elements fluorine, zinc, strontium, silicon, iron, rubidium, caesium and platinum. Finally the composition contains glycosaminoglycans, citrate and water. Nothing is known about how MCHC is manufactured.

SUMMARY OF THE INVENTION

The object of the invention is to provide an ossein hydroxyapatite compound (OHC) and a method for its production. A further object is to provide pharmaceutical compositions that contain OHC and that are suited to stimulation (proliferation) of chondrocytes and osteoblasts and hence to the prophylaxis and treatment of osteoarthritis and osteoporosis and healing bone fractures, cartilage defects and bone defects.

OHC was found to have a specific effect on the metabolism of bones and cartilage, for it contains organic components in non-denatured state and also inorganic components in physiologically balanced proportions. Application of OHC ensures that the human and animal organism is supplied with substances essential to the skeletal system (non-collagenic bone-specific peptides, locally active bone and cartilage cell regulating factors, calcium and phosphate). OHC supports bone metabolism with an organic ossein matrix of collagens and essential, bone-specific, non-collagenic peptides and proteoglycans, promotes bone regeneration and enhances incorporation in the bones of the inorganic components of hydroxyapatite that are embedded in the ossein matrix. Furthermore, OHC stimulates the body's cartilage repair mechanisms and protects cartilage tissue from degeneration.

OHC exhibits a characteristic biological action on osteoblasts, the cells responsible for generating bone tissue. OHC intensifies the proliferation and metabolism of osteoblasts and furthermore promotes differentiation of non-specific mesenchyme cells to chondroblasts or osteoblasts. Thus OHC is a new curative for bone diseases of differing genesis, for example in primary and secondary osteoporoses and in healing bone fractures and bone defects and for optimization of prosthesis. It is clear from the cytobiological properties mentioned, which were confirmed in vivo pharmacologically in animals and clinically in humans, that OHC is markedly superior to conventional calcium preparations and to all bone meals. OHC offers a real alternative to the pure bone resorption inhibitors within therapeutical products for osteoporosis such as estrogens and calcitonins, as OHC not only inhibits bone resorption but above all promotes bone growth. OHC is distinguished from the existing therapeutical products that likewise stimulate bone metabolism, e.g. sodium fluoride and diphosphonates, by the fact that it produces markedly fewer side effects, being free, for instance, of gastrointestinal side effects and aching joints. Diphosphonates have a very narrow therapeutical range, whereas OHC is virtually nontoxic.

In addition OHC exerts a biological action on chondrocytes, which are responsible for the formation and resorption of the cartilage tissue. Without loss of their phenotype chondrocytes are stimulated by OHC to proliferation and increase of their metabolism, as well as protected against iatrogenic noxae such as corticosteroids. Besides, OHC promotes differentiation of unspecific mesenchyme cells to chondrocytes and thus promotes chondroid metaplasia, a process that plays a major part in the regeneration of cartilage tissue.

OHC is therefore outstandingly useful in the treatment of osteoarthritis, where there is a decrease in the number of chondrocytes and their metabolic activity and where regeneration of the cartilage would demand ordered chondroid metaplasia. OHC is furthermore suited to treating osteoporosis and supporting the healing of bone fractures and of bone and cartilage defects.

The biological activity of OHC can be identified in vitro as, for example, (a) stimulation of the DNA synthesis of osteoblasts, chondrocytes and fibroblasts, (b) stimulation of the protein synthesis of chondrocytes and fibroblasts, (c) selective stimulation of the collagenic total synthesis of chondrocytes in comparison to stimulation of total protein synthesis, (d) induction of the synthesis of proteins x and y in chondrocytes, and (e) promotion of the differentiation of nonspecific mesenchyme cells to chondrocytes or osteoblasts.

In the stimulation of collagenic total synthesis the ratio of collagen types I and II remains unchanged in chondrocyte cultures over 24 hours, thereby preserving the phenotype of the chondrocytes over this period.

The biological effect on DNA synthesis is determined in a commonly used manner by measuring the stimulation of the $^3$H-thymidine uptake by cell lines, for example 3T3 fibroblasts; see Jimenez de Asua et al., Proc. Nat. Acad. Sci. U.S.A., Vol. 72 (1975), 2724-2728. This is a commonly used biological technique for identifying mitogenic substances. It is advantageous to use cell lines in this identification method as cell lines are easy to culture.

This test method is based on the consideration that untransformed fibroblasts in the cell culture exhibit two extreme growth states. In the quiescent state the cells are in the $G_0$–$G_1$ phase and therefore do not divide. In addition there is the state of active proliferation. Transition from the quiescent to the proliferating state can be regulated by the concentration of essential nutrients, serum or other growth promoting factors. OHC contains such growth promoting factors. The latter are soluble in neutrally buffered physiological solvents such as phosphate buffered saline (PBS) or physiological saline, and they exert a high stimulatory, dose related uptake of $^3$H-thymidine by quiescent 3T3 fibroblasts.

The frequently used method of sterilizing foodstuffs and pharmaceutical preparations by irradiation with gamma rays does not diminish the biological activity of OHC as measured by the stimulatory effect on the $^3$H-thymidine uptake of 3T3 fibroblasts.

This experimental system can also be used to determine cell-specific stimulation of osteoblast DNA synthesis. Osteoblast populations obtained by sequential enzyme digestion from rat calvaria are used. The osteoblast populations represent various stages in maturity of the osteoblasts; populations I to III are regarded as being of preosteoblast type, populations IV to VII as osteoblast type and population L as quiescent osteoblast type cells or osteocytes.

Neutrally solubilized OHC components have a dose dependent stimulatory effect on the osteoblasts of populations V and VI. Proliferation of primary cultures of rat fibroblasts assayed in parallel is not stimulated. It follows from these experimental findings that the neutrally solubilized OHC components exhibit bone cell specific activity.

The biological effect on protein synthesis is determined in a commonly used manner by measuring the stimulation of the L-(5-$^3$H)-proline uptake of cells, for example cell lines such as 3T3 fibroblasts, or of human foreskin fibroblasts. This method is based on the consideration that the protein synthesis of stimulated cells increases. If L-(5-$^3$H)-proline is offered to the stimulated cells in cell culture medium they incorporate it into the newly synthesized proteins. After a set incubation period the amount of the radioactivity uptake is measured, being a measure of the stimulatory effect. OHC contains neutrally solubilized components which exert a high stimulatory, dose dependent effect on protein synthesis in 3T3 fibroblasts and human foreskin fibroblasts.

The alkaline phosphatase assay is conducted in the manner recommended by the Deutsche Gesellschaft für klinische Chemie, Z. Klin. Chem. and Klin. Biochem., Vol. 8 (1970), 658; Vol. 9 (1971), 464; and Vol. 10 (1972), 182. Phosphatase activity is assayed for quality control purposes at each stage in the method of the invention.

Table I summarizes the composition of OHC (values obtained from around 150 batches) determined by analysis.

TABLE I

| Organoleptic Test | Fine to slightly granular, beige-gray powder with faint natural odor |
|---|---|
| Identity | Calcium and phosphatase identified Collagen identified |
| Water Content | <7% |
| Total ash | 51.3–62.7% |
| Calcium | 19.2–23.6% |
| Phosphorus | 8.9–10.9% |
| Collagen | 23.4–28.6% |
| Non-collagenic Proteins/Peptides | 7.2–10.8% |
| Trace Elements | F, Na, K, Mg, Fe, Zn, Cu and Ni identified |
| Phosphatase Activity | 0.5–15 mE/mg |
| Anomalous Toxicity | No signs of intolerance |
| Total Microbial Content | <10$^4$/g |
| Yeasts | <10$^2$/g |
| Enterobacteriaceae | <10$^2$/g |

TABLE I-continued

| Specific Microbe Species | Absent/g |
|---|---|

DESCRIPTION OF THE INVENTION

In accordance with the invention the following steps are carried out to produce OHC:

First bones are removed from fetal to approximately 12 month old mammals that have been examined by official veterinarians. After their removal the clean bones are quickly deep frozen and kept at around $-20°$ to $-30°$ C. until needed; see FIG. 1, box 1. Before being processed further the bones are checked to see that they are still fresh, which can be determined by their odor and color. The bones are also checked to see that they are clean and actually are the bones required. If necessary the bones are checked for size and shape against a manual of the anatomy of domestic animals. Any remains of meat, tendons and cartilage are also removed.

If there is any doubt about the identity of the animal, the species may also be determined with the help of usual immunological reactions, for example precipitation.

The bones are then crushed in a breaker mill to a particle size of approx. 1 cm maximum (see FIG. 1, box 2). The bone particles are next dried under reduced pressure at 20° to 80° C. until their residual water content is around 10% maximum or between around 10 to 25% (see FIG. 1, boxes 3a and 3b). The bone material obtained is then brought to a pH of approx. 5.0 to 5.5 using an acid such as hydrochloric acid, phosphoric acid, acetic acid, formic acid or citric acid. Next the bone material is dehydrated and degreased using a hydrophilic and lipophilic solvent to a maximum residual water content and residual fat content of about 5% or else first dehydrated to a maximum residual water content of about 5% using a hydrophilic solvent at 20° to 80° C. and then degreased to a residual fat content of about 5% maximum using a lipophilic solvent at 20° to 80° C. (see FIG. 1, boxes 4a and 4b).

The resulting dehydrated and degreased bone material is then dried further under reduced pressure at 20° to 80° C., for example in a vortex, until a maximum solvent content of about 1% is reached (see FIG. 1, box 5).

Depending on the application envisaged the bone material obtained is then pulverized in the normal manner in grinding and screening machines into powders of various grain sizes from about 50 to 300 microns (see FIG. 1, box 6).

If the number of microbes in the bone material exceeds around 10,000 per gram, the bone material is sterilized in the usual way, e.g. by treating it with ethylene oxide or irradiating with gamma rays (see FIG. 1, boxes 10 to 12). OHC suitable for producing pharmaceutical drugs is obtained (see FIG. 1, box 13).

In an alternative version of the method of the invention, the mammalian bones as described above are crushed to a maximum particle size of approx. 1 cm, for example in a breaker mill (see FIG. 2, box 2). The particles of bone are then brought to pH 5.0 to 5.5 with an acid. Next they are dehydrated and degreased to a maximum residual water and fat content of about 5% using a hydrophilic and lipophilic solvent, or first dehydrated with a hydrophilic solvent at 20° to 80° C. to a maximum residual water content of about 5% and then degreased with a lipophilic solvent at 20° to 80° C. to a maximum residual fat content of about 5% (see FIG. 2, boxes 3a and 3b).

The resulting dehydrated and degreased bone material is then dried further under reduced pressure at 20° to 80° C., for example in a vortex current, until a maximum solvent content of about 1% is reached (see FIG. 2, box 4). If necessary, the bone material may be further processed as described above (see FIG. 2, boxes 5 through 11). The OHC suitable for manufacturing pharmaceutical drugs is obtained (FIG. 2, box 12).

Preferred bones for use in the method of the invention as detailed above are long bones such as the humerus, femur, tibia, radius and ulna, os metacarpale or os metatarsale. Furthermore, bones from bovine calves (Bos taurus) are preferably used.

It is evident that to prevent the product from becoming denatured it is necessary in each case to reduce the drying and degreasing temperature as the moisture and solvent content falls. As already mentioned, a maximum temperature of 80° C. is used for dehydrating and drying. As the water and solvent content drops, the temperature is reduced and the operation is performed very rapidly.

During the dehydration and drying operation the pressure is approx. 400 mbar at maximum.

Typical examples of suitable lipophilic solvents are acetone, trichloroethylene, methylene chloride and low boiling petroleum ether. Typical examples of suitable hydrophilic solvents are acetone, ethanol and isopropanol.

The resulting OHC can be confectioned in conventional manner into pharmaceutical products for oral administration such as granulates, filmcoated tablets, capsules, coated pills, powders or suspensions. The daily doses are 0.6 to 10 g, divided into two or three individual doses. The unit of dose is 200 to 4000 mg.

To produce granules OHC is blended with fillers and flavorings, wetted with water, granulated and dried.

To produce filmcoated tablets OHC is granulated in a moist state, dried and then screened. Flowance agents, lubricants and disintegrating agents are admixed. The mixture, now ready for molding, is tableted and then coated with a thin colored lacquer.

To produce coated pills OHC is granulated in moist state, dried and screened. Then usual tableting auxiliaries are added and the pill kernels are molded. The kernels are separated, given a white topcoat, colored and polished.

To produce powders OHC is processed into crustaceous granules and then aromatized and screened.

To produce suspensions OHC is suspended in molasses along with auxiliaries that enhance viscosity. The suspension is colored and aromatized and then conserved.

DESCRIPTION OF THE DRAWINGS

FIG. 5 shows stimulation of $^3$H-thymidine uptake in bovine chondrocytes as a function of the dose of OHC 34/4. The abscissa gives the concentration in the tested samples in $\mu$g/ml culture medium, the ordinate the $^3$H-thymidine uptake in cpm $\times 10^4$.

In the cytobiological system investigated only OHC, and PMC and Lencoll® are active.

1 g of each of the investigated products was extracted with 10 ml of PBS; aliquots of centrifuged supernatants were tested.

Figure 10:
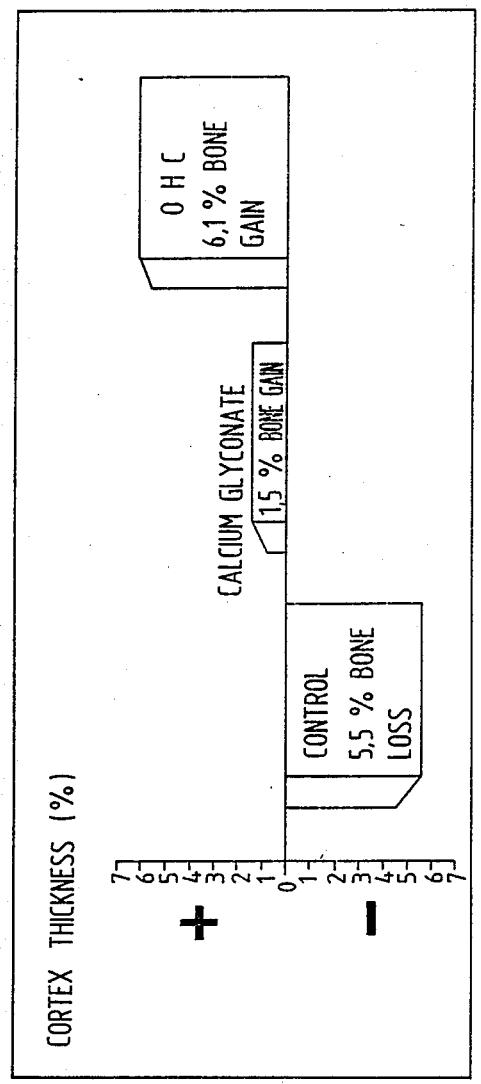

FIG. 10 shows the percentage change in bone cortex thickness after 14 months of treatment with vitamin D$_2$, calcium gluconate and with OHC. By comparison with vitamin D$_2$ there is 11.6% gain when OHC is used.

Figure 11:
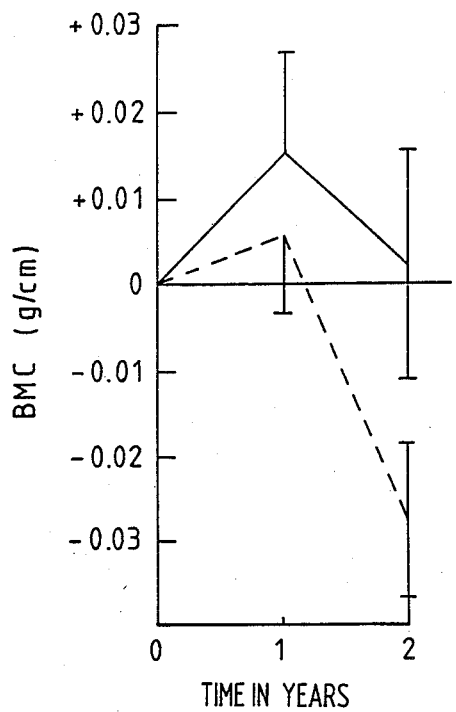

FIG. 11 illustrates the mean change in radius mineral content BMC in g/cm in patients treated with OHC (_) and controls (—) over a two year period. Standard deviations are indicated by the bars.

Figure 12:
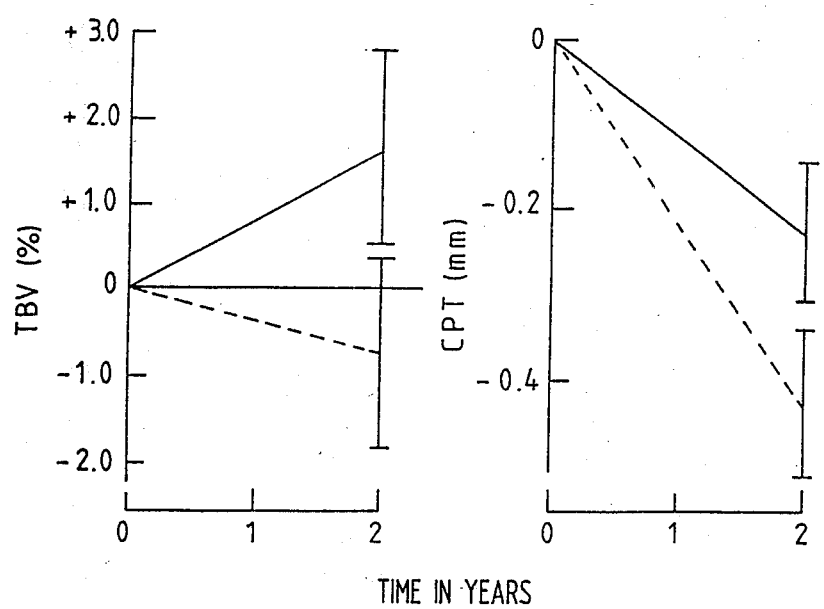

FIG. 12 shows mean changes in trabecular bone volume (TBV) and cortex thickness of the iliac crest (CPT) in patients treated with OHC (_) and controls (—) in a period of two years. Standard deviations are indicated by the bars.

In FIG. 13 the ordinate shows the uptake of $^3$H-Thymidine in cpm, and the abscissa the concentration in the sample investigated in $\mu$g/200 ml culture.

DESCRIPTION OF THE PREFERRED EMBODIMENTS

The present invention is illustrated in more detail by the examples.

EXAMPLE 1

Preparation of OHC (Method 1)

Long bones (humerus, femur, tibia, radius and ulna, os metacarpale and os metatarsale) from approximately 3 month old bovine calves (bos taurus) are used as the starting material for producing OHC.

The animals are examined by official veterinarians. Then they are slaughtered and the bones removed. After boning the clean bones are quickly deep frozen and stored at −20° to −30° C. until further treatment; see FIG. 1, box 1).

Before they are processed further, the bones are checked for freshness (recognizable by their odor and color), for cleanness and to ensure that they actually are the bones required. Any meat, tendon and cartilage remains are removed.

In the first step of the method 1600 kg (1 batch) of frozen bones are crushed in a breaker mill made of stainless steel with 20 mm screen perforations. The size of the particles of crushed bone is approx. 1 cm. The temperature of the bones is maintained below 0° C. during crushing; see FIG. 1, box 2.

Figure 1:
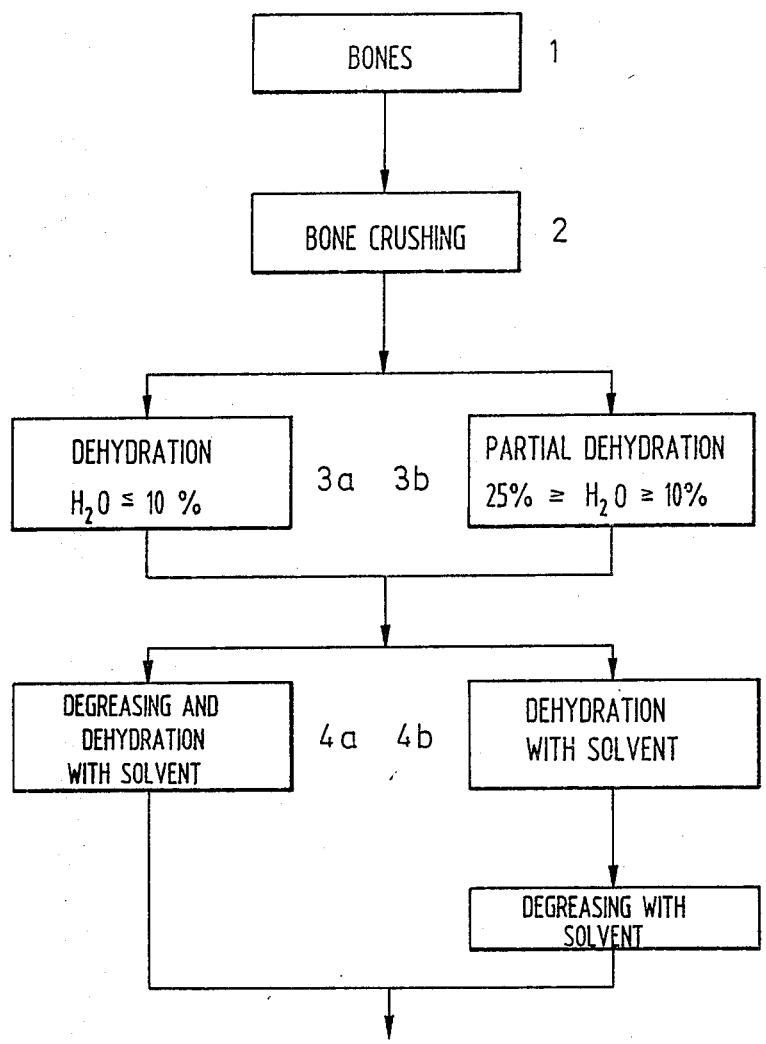
FIG. 1 shows the scheme for preparing OHC as in Example 1.
Figure 1:
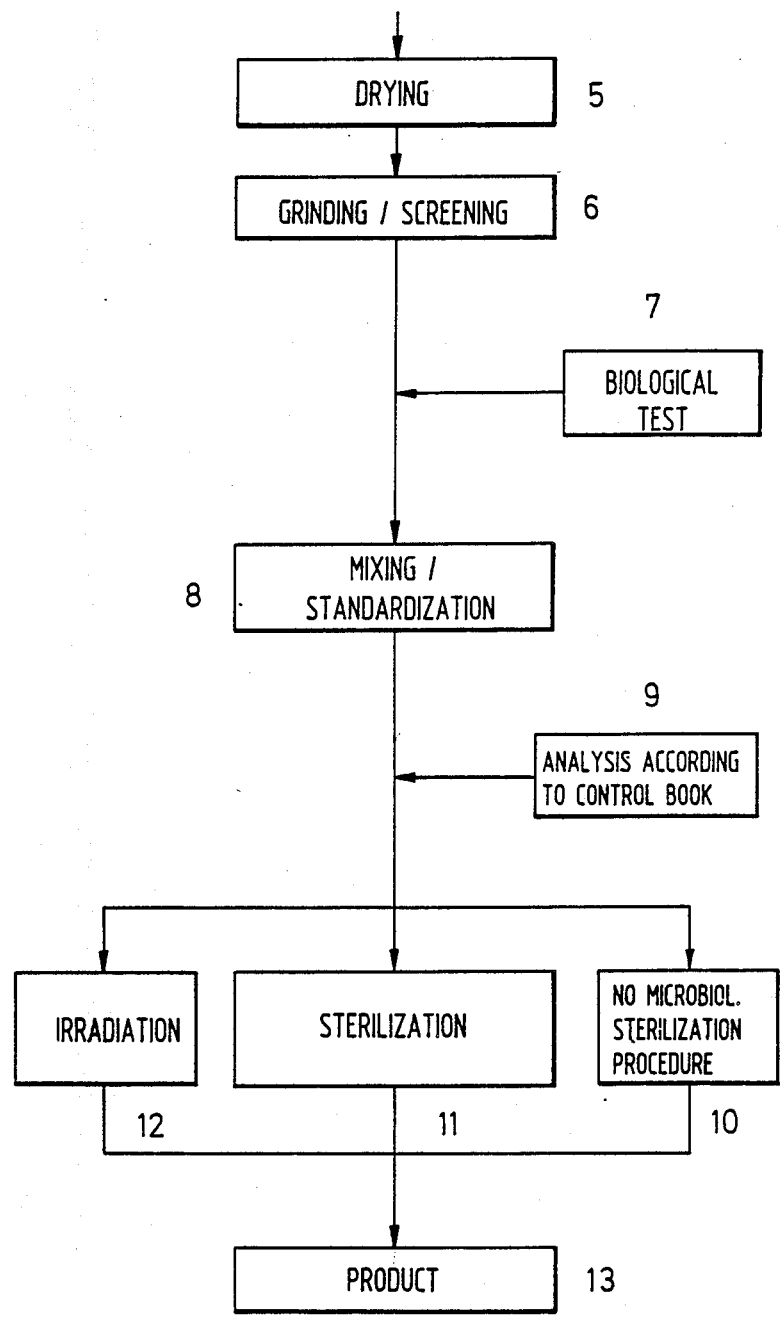
Figure 2:
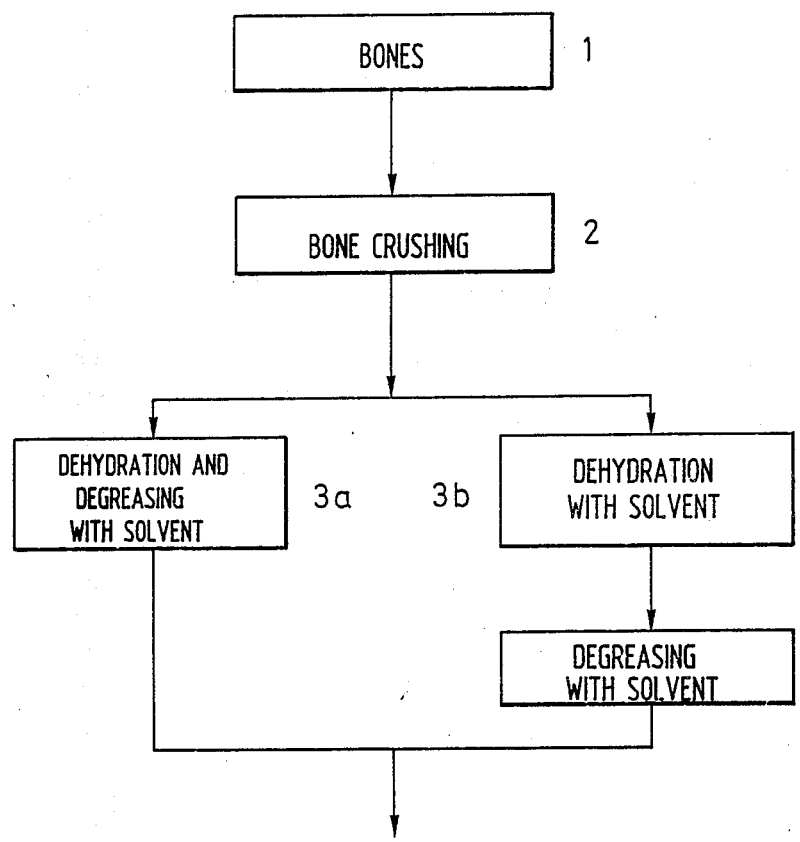
FIG. 2 shows the scheme for preparing OHC as in Example 2.
Figure 2:
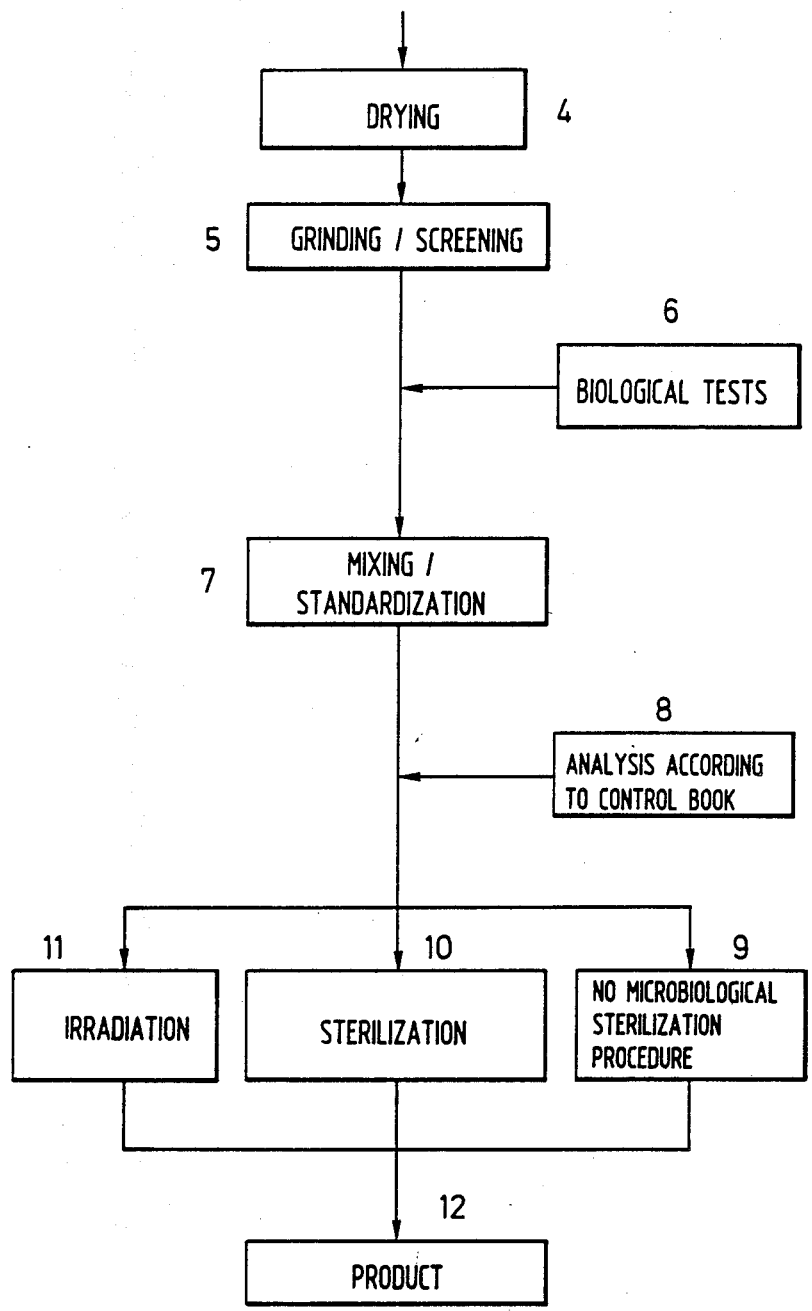

Next the crushed bones are dehydrated in a stainless steel blade drier at a pressure of 0.97 to 0.98 bar. The hot water is initially at a temperature of around 90° C. and is lowered to around 40° C. in the course of drying. As soon as no more water distills over into the condensate collector (some 10 hours after drying commences), the heating is discontinued and the bone composition is dried further under reduced pressure, until the residual water content is either a maximum of about 10% (see FIG. 1, box 3a) or 10 to 25% (FIG. 1, box 3b). In this latter drying operation the temperature of the bone composition should not exceed 40° C.

The dried bone composition is then brought to pH 5.0 to 5.5 with citric acid. The dried bone composition is now dehydrated once more at 80° to 20° C. and the lipids removed. For this either acetone is used as the hydrophilic and lipophilic solvent or else the dried bone composition is first dehydrated with acetone at temperatures from 20° to 80° C. and then degreased using trichlorethylene at 20° to 80° C. in a second operation. A bone composition is obtained in which the residual water content and residual fat content is 5% maximum (see FIG. 1, boxes 4a and 4b). Solvent residues are then removed in a vortex current at 20° to 80° C. and 90 mbar. The residual solvent content is about 1% (see FIG. 1, box 5).

The resulting bone composition is ground in a hammer mill in a 2×20 mm slotted sieve and screened on a screening machine in which the upper sieve has a mesh size of 2.4 mm and whose lower sieve has a mesh size of 0.34 mm. The material remaining on the 2.4 mm sieve is discarded, and that screened through the 0.34 mm sieve is used further. It is ground once again in a grinding machine with a 0.8 mm perforated screen insert and screened on a screening machine having one sieve with a mesh size of 0.74 mm and another with a mesh size of 0.34 mm. The material remaining on the 0.74 mm sieve is discarded. The material screened through the 0.34 mm sieve is collected and ground once more in a grinding machine with a 0.8 mm perforated screen insert. It is then screened in the manner described above. Finally the powder is collected and screened using a sieve with a mesh size of 0.25 mm and ground in a grinding machine with a 0.5 mm perforated screen insert. All the powder is then passed through a screen with a mesh size of 0.25 mm (see FIG. 1, box 6).

Table II provides a summary of the analytical values of the resulting OHC powder.

TABLE II

| Organoleptic Test | Fine to slightly granular, beige-gray powder with faint natural odor | In order |
|---|---|---|
| Identity | Calcium and phosphatase identified | In order |
| | Collagen identified | In order |
| Water Content | <7% | 6.3% |
| Total ash | 51.3–62.7% | 56.2% |
| Calcium | 19.2–23.6% | 21.57% |
| Phosphorus | 8.9–10.9% | 9.71% |
| Collagen | 23.4–28.6% | 26.4% |
| Non-collagenic Proteins/Peptides | 7.2–10.8% | 9.0% |
| Trace Elements | F, Na, K, Mg, Fe, Zn, Cu and Ni identified | In order |
| Phosphatase Activity | 0.5–15 mE/mg | 3.9 mE/mg |
| Anomalous Toxicity | No signs of intolerance | In order |
| Total Microbial Content | $<10^4$/g | Approx. 300 |
| Yeasts/Molds | $<10^2$/g | Absent |
| Enterobacteriaceae | $<10^2$/g | Absent |
| Specific Microbe Species | Absent/g | Absent |

If the analysis shows that the OHC composition contains more than 10,000 microorganisms per gram, the composition is either sterilized by treating it with ethylene oxide or by irradiation with gamma rays (see FIG. 1, boxes 10–12).

OHC suitable for the production of pharmaceutical compositions is obtained (see FIG. 1, box 13).

EXAMPLE 2

Preparation of OHC (Method 2)

A crushed bone composition with a maximum particle size of 1 cm is prepared as in Example 1. This bone composition is then brought to pH 5.0 to 5.5 with citric acid and further treated as in Example 1.

An OHC composition having the analytical values outlined in Table III is obtained.

TABLE III

| Organoleptic Test | Fine to slightly granular, beige-gray powder with faint natural odor | In order |
|---|---|---|
| Identity | Calcium and phosphatase identified | In order |
| | Collagen identified | In order |
| Water Content | <7% | 6.6% |
| Total ash | 51.3–62.7% | 56.07% |
| Calcium | 19.2–23.6% | 21.33% |
| Phosphorus | 8.9–10.9% | 9.95% |
| Collagen | 23.4–28.6% | 26.2% |
| Non-collagenic Proteins/Peptides | 7.2–10.8% | 8.8% |
| Trace Elements | F, Na, K, Mg, Fe, Zn, Cu and Ni identified | In order |
| Phosphatase Activity | 0.5–15 mE/mg | 5.4 mE/mg |
| Anomalous Toxicity | No signs of intolerance | In order |
| Total Microbial Content | $<10^4$/g | Approx. 10 |
| Yeasts/Molds | $<10^2$/g | Absent |
| Enterobacteriaceae | $<10^2$/g | Absent |
| Specific Microbe Species | Absent/g | Absent |

EXAMPLE 3

Stimulation of $^3$H-Thymidine Uptake in 3T3 Fibroblasts by OHC

Swiss mouse 3T3 fibroblasts (Flow Laboratories) are cultured in DMEM (Dulbecco's modified Eagle's medium, boehringer Mannheim). The medium is supplemented with 100 units/ml penicillin, 100 mg/ml of streptomycin (both from Boehringer Mannheim) and 3.7 g of NaHCO$_3$/liter (Merck, Darmstadt), after being first brought to pH 6.6 with CO$_2$ before sterile filtration. In addition the culture is supplemented with 10% fetal calf serum (Boehringer Mannheim) for cell culturing. The subconfluent cultures are grown in 90 mm petri dishes at 37° C. under 5% CO$_2$ pressure and the cells are subcultured twice a week with an initial seed of $4 \times 10^4$ cells per 10 ml of culture medium per petri dish. In each of the investigations detailed below cells from passages 3 through 20 are used.

The assay for $^3$H-thymidine uptake is performed in the manner described by L. Jimenez de Asua et al. (Proc. Natl. Acad. Sci. U.S.A., Vol. 72 (1975), pp. 2724-2728). Swiss mouse 3T3 fibroblasts from the stock cultures described above are trypsinized using a sterile solution of 0.05% trypsin/0.02% EDTA. The cells are resuspended in DMEM/10% fetal calf serum at a concentration of $4 \times 10^4$ cells/ml. 1 ml aliquots of cell suspension are plated onto 1.9 cm$^2$ microtiter plates. The cells are incubated for a further 4 days without change of medium, and confluent monolayers of quiescent, nonproliferating cells are established. The medium is then sucked off and replaced with 1 ml of fresh culture medium without fetal calf serum, with samples for testing also being added.

1 g of OHC prepared as in Examples 1 or 2 is suspended in 10 ml of phosphate buffered saline without Mg and Ca (0.2 g KCl, 8 g NaCl, 2.7 g NaHPO$_4$.12H$_2$O, 0.2 g KH$_2$PO$_4$ per liter). After 2 hours of shaking at room temperature the samples are centrifuged for 15 mins at $2000 \times g$.

Aliquots of 2-500 µl of the clear supernatants obtained after centrifugation containing the neutrally solubilized OHC components are then added to the 3T3 fibroblast cultures obtained above.

For measuring blanks an identical quantity of fresh culture medium is merely added to the cultures. As a positive control 2-200 µl of fetal calf serum are added. The cultures for assay are finally incubated for 20 hrs at 37° C. under 5% CO$_2$ pressure and then pulsed with $^3$H-thymidine. The cells are radioactively labeled by adding 10 µl/ml of culture medium per well of a sterile aqueous thymidine solution containing 1 µCi (methyl-$^3$H)thymidine (Amersham, U.K.) and 0.9 µg methyl thymidine (Sigma, U.S.A.). After the $^3$H-thymidine has been added there is a further 4 hr incubation period under the conditions indicated above.

The samples are then processed for scintillation counting. The culture medium is sucked off and the cell layer washed with 0.5 ml of a 0.02% EDTA/PBS solution. The cells are trypsinized as described above until they become fully detached. The suspended cells are processed in a microtiter Dynatech multimash apparatus where they are automatically transferred to glass microfiber filters (Whatman 934-AH). The apparatus is programed as follows:

(1) PBS wash; (2) precipitation with 5% trichloroacetic acid (Merck, Darmstadt); (3) ethanol fixation. The glass microfiber filters are dried and transferred to scintillation vials. 3 ml of liquid scintillation cocktail are added (7 g of Permablend Packard in 1 liter of Triton X-100/toluene in a 1:3 ratio; Merck, Darmstadt), and the radioactivity of the samples is measured as disintegrations per minute in an LKB-Wallac 1217 Rackbeta liquid scintillation counter.

Figure 3:
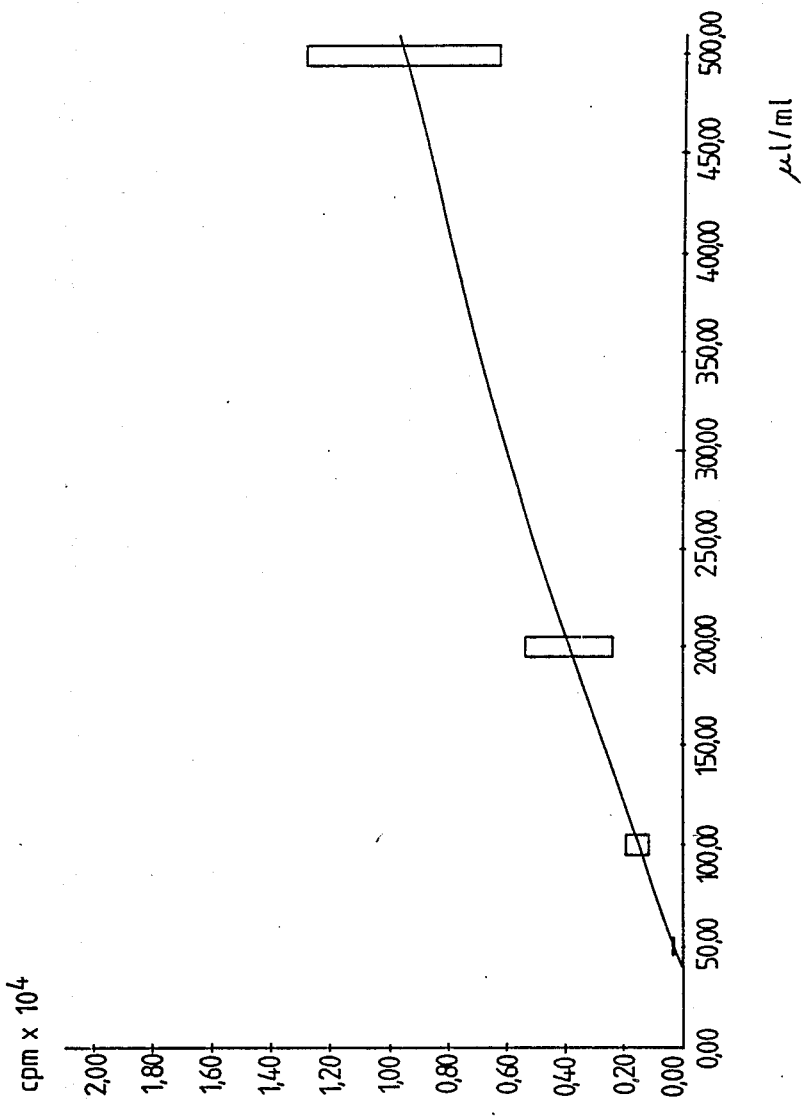
FIG. 3 shows stimulation of $^3$H-thymidine uptake in 3T3 fibroblasts by an OHC extract. The abscissa shows the concentration of OHC extract in $\mu$l/ml culture medium. The ordinate shows the uptake of $^3$H-thymidine in cpm $\times 10^4$. The bars give the standard deviations for the mean values from nine measurements; corr. coeff. 0.917.

Maximal stimulation with OHC only reaches about half the maximum stimulation achieved with fetal calf serum. However, it should be remembered that the fetal calf serum contains around 60 times as much total protein as the OHC extracts. Thus, uptake of $^3$H-thymidine is stimulated by the OHC extracts used to a significantly greater degree than when fetal calf serum is used. The measurement results obtained using OHC are summarized in FIG. 3.

The system of assay described can also be used to measure the quality of the OHC compositions obtained in accordance with Examples 1 or 2. When fetal calf serum is used as a positive control, on the one hand as an internal check on the cytobiological assay system and on the other as a reference for the values obtained with the OHC samples, it is possible to define and express an activity unit for the characterization of the biological activity of the OHC compositions. This allows standardization of the biological activity of OHC compositions.

EXAMPLE 4

Figure 4:
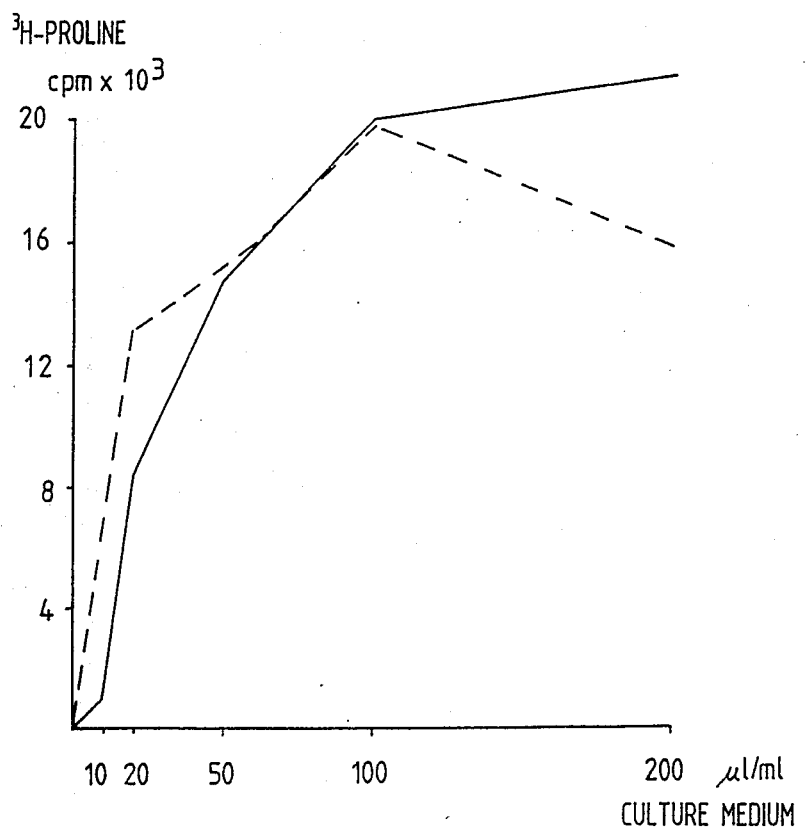
FIG. 4 shows stimulation of L-(5-$^3$H) proline uptake in 3T3 fibroblasts by fetal calf serum (—) and by OHC components (_). The abscissa gives the concentration in the sample tested in $\mu$l/ml culture medium; the ordinate indicates the uptake of L-(5-$^3$H) proline in cpm $\times 10^3$.

Stimulation of L-(5-$^3$H)Proline Uptake in 3T3 Fibroblasts and Human Foreskin Fibroblasts by OHC The proline uptake of the cultured cells can be measured as in Example 3, but using L-(5-$^3$H)proline instead of $^3$H-thymidine in the cell culture system already described. This assay determines the rate of protein synthesis by the cultured cells, and by measuring and quantifying the radioactivity absorbed by the cells the biological activity of the OHC compositions can be determined. FIG. 4 shows the stimulation of L-(5-$^3$H)proline uptake in 3T3 fibroblasts by OHC.

FIG. 4 reveals that the OHC composition substantially increases the protein synthesis rate in the cells investigated.

EXAMPLE 5

The Effect of Neutrally Solubilized Components of OHC on Bovine Chondrocyte Cultures Chondrocytes are isolated from the epiphyseal cartilages of fetal calves in the usual manner. 50,000 cells are grown subconfluently for 4-6 days, in each case with 1 ml of F12 medium supplemented with 10% fetal calf serum. As in Example 3 the resulting cell cultures are treated with the OHC compositions 34/4 obtained in accordance with Examples 1 or 2. The cells are then pulsed with $^3$H-thymidine as in Example 3 and the incorporated radioactivity is measured.

FIG. 5 provides a summary of the results from the first test run. The uptake of $^3$H-thymidine by the bovine chondrocytes is shown in response to the dose of substances OHC 34/4.

Figure 7:
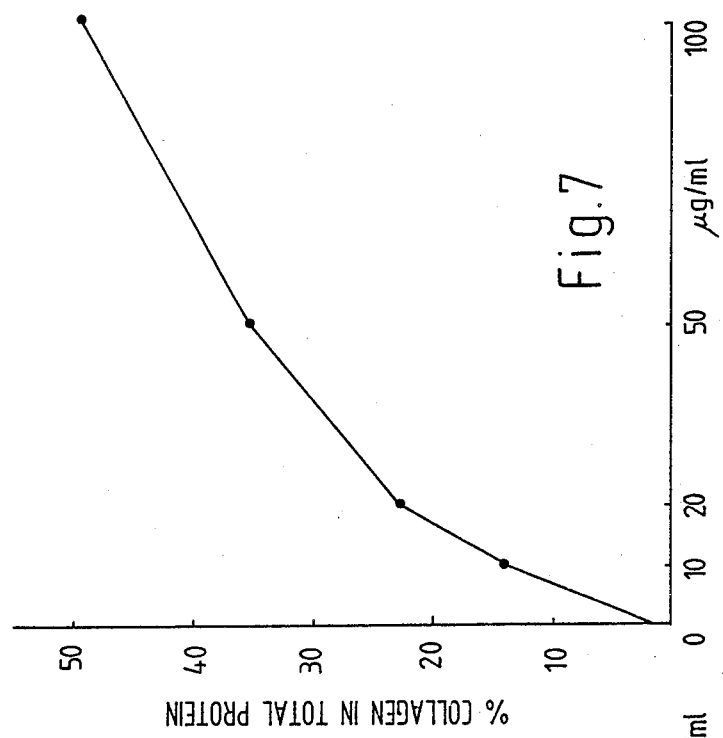
FIG. 7 shows the percentage increase in collagen content in the total protein as a function of the OHC dose.
Figure 6:
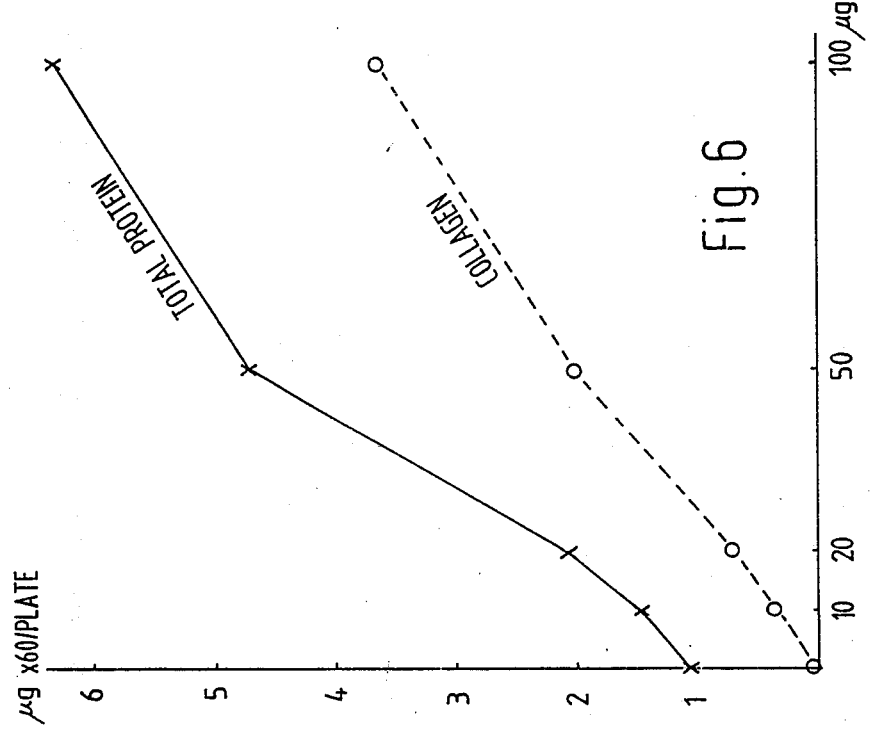
FIG. 6 shows stimulation of the collagen synthesis and total proteins of chondrocytes in monolayer cultures as a function of OHC concentration. The abscissa gives the $\mu$g amount of active assay protein used per ml culture. The ordinate indicates the $\mu$g amount of newly synthesized protein x—x and collagen o—o respectively for each culture batch.

It is evident from FIGS. 6 and 7 that the investigated OHC 35/4 stimulates total protein synthesis and the rate of collagen synthesis.

34/4 and 35/4 denote batch serial numbers.

EXAMPLE 6

The Effect of Neutrally Solubilized Components of OHC on Bone Cell Populations in Vitro Essentially as described by Cohn et al. (Simmons and Kanin (ed.), Skeletal Research, an Experimental Approach, Academic Press, New York, San Francisco, London, pp. 3-20), various bone cell populations are isolated by sequential time-dependent enzymatic digestion procedure from 1 day old Wistar rat calvaria, with the exception that hyaluronidase 0.05% is used as an additional enzyme along with collagenase and trypsin to liberate the cells from the bone tissue.

The various cell populations liberated during 20 minutes of digestion are designated with roman numerals corresponding to the order in which the individual cell fractions are obtained. The first cell population to be liberated from the calvaria is called I, while the last cell fraction, liberated in the course of 1 hour of digestion, is labeled L. Functional tests suggest that populations I through III probably represent cells of the osteoprogenitor cell pool (preosteoblast like). Cell populations IV through VI exhibit features with osteoblast-like character, and those designated VII and L can be regarded as quiescent osteoblast-like cells, or perhaps osteocyte-like cells.

10 ml of a suspension of $1.5 \times 10^5$ cells/ml MEM medium (with Earle's salts) supplemented with 10% fetal calf serum are plated in 250 ml tissue culture flasks. After incubation for 9–10 days at 37° C. under 5% $CO_2$ pressure confluent cell layers are obtained, which are brought into suspension with trypsin 0.2%. The cells are harvested by centrifugation at $400 \times g$ for 7 mins. The resulting cell pellet is resuspended in MEM medium supplemented with 20% fetal calf serum and 10% DMSO and the suspensions are then frozen away in liquid nitrogen until further use.

The individual, frozen bone cell populations are carefully brought up to 37° C. and taken up in 40 ml of MEM supplemented with 20% fetal calf serum. They are centrifuged for 7 mins at $400 \times g$ and the resulting cell pellets are resuspended in fresh medium supplemented with 10% fetal calf serum and plated out in 96 well microtiter plates at a density of $7-10 \times 10^3$ cells per well. The cells are cultured for two days. On the third day the culture medium is replaced by a medium containing either 1% or 2% fetal calf serum. After incubation for 24 hrs the medium is once again replaced with fresh medium containing 1% or 2% fetal calf serum, 0.5 $\mu$Ci $^3$H-Thymidine/ml and neutrally solubilized OHC components in various concentrations. Appropriate amounts of PBS are added to the control cultures.

To establish that the various bone cell cultures actually do respond to a mitogen, experiments are performed using EDGF (Epidermal Growth Factor). The bone cell cultures are incubated for 24 hrs under the conditions stated above with the medium containing the $^3$H-thymidine. The amount of $^3$H-thymidine incorporated is then measured as in Example 3.

The experimental results are summarized in Table IV, where each value represents the average obtained from five runs and is indicated along with the standard deviation. The OHC components dissolved in PBS are added to the culture media in amounts of 5–50 $\mu$liters for a total culture medium volume of 200 $\mu$liters.

TABLE IV

| Bone cell populations | $^3$H-Thymidine incorporation for stimulation with neutrally solubilized OHC components V and X in the presence of (cpm/well ± standard deviation) ||
|---|---|---|
| | 1% FCS* | 2% FCS* |
| P-I | | |
| Control (PBS) | 19022 ± 1630(5) | 27656 ± 841(5) |
| Op V | 11070 ± 1160(5) | 12394 ± 195(5) |
| Op X | 11800 ± 508(5) | 12678 ± 884(5) |
| P-II | | |
| Control | 19023 ± 552(5) | 25103 ± 344(5) |
| Op V | 15440 ± 491(5) | 14910 ± 611(5) |
| Op X | 13161 ± 491(5) | 13425 ± 940(5) |
| P-III | | |
| Control | 12473 ± 582(5) | 15159 ± 588(5) |
| Op V | 8179 ± 433(5) | 10105 ± 600(5) |
| Op X | 6735 ± 455(5) | 9676 ± 436(5) |
| P-IV | | |
| Control | 16482 ± 750(5) | 21006 ± 711(5) |
| Op V | 9445 ± 481(5) | 11388 ± 649(5) |
| Op X | 6945 ± 178(5) | 10356 ± 539(5) |
| P-V | | |
| Control | 18298 ± 774(5) | 22677 ± 176(5) |
| Op V | 14380 ± 746(5) | 16115 ± 261(5) |
| Op X | 14866 ± 250(5) | 18330 ± 296(5) |
| P-VI | | |
| | 25789 ± 966(5) | 37205 ± 2553(5) |
| Op V | 23424 ± 1026(5) | 28168 ± 711(5) |
| Op X | 23346 ± 1239(5) | 32107 ± 422(5) |
| P-VII | | |
| | 19405 ± 827(5) | 26369 ± 1236(5) |
| Op V | 30189 ± 1327(5) | 41293 ± 1769(5) |
| Op X | 37498 ± 994(5) | 44817 ± 728(5) |
| P-L | | |
| | 13378 ± 396(5) | 18654 ± 491(5) |
| Op V | 18677 ± 523(5) | 26816 ± 1027(5) |
| Op X | 28488 ± 1241(5) | 33411 ± 1220(5) |

*FCS = fetal calf serum

It is evident from Table IV that the neutrally solubilized OHC components stimulate the proliferation of bone cell populations V and VI as against the control cultures treated with PBS. Bone cell populations I and VII do not show any reaction. The results are reproduced in graphic form in FIG. 13.

EXAMPLE 7

Table V gives a summary of the results of experiments in which the action of neutrally solubilized OHC components (OHC X) was assayed on rat skin fibroblasts.

TABLE V

| $^3$H-Thymidine incorporation of rat skin fibroblasts in response to various concentrations of OHC X ||
|---|---|
| | $^3$H-Thymidine incorporation (ccm/well ± standard deviation) |
| no FCS | 450 ± 29 |
| +15 $\mu$l PBS | 485 ± 38 |
| +7.5 $\mu$l OHC X | 343 ± 18 |
| +15.0 $\mu$l OHC X | 582 ± 42 |
| +30.0 $\mu$l OHC X | 618 ± 16 |
| 1% FCS | 917 ± 85 |
| +15 $\mu$l PBS | 921 ± 33 |
| +7.5 $\mu$l OHC X | 606 ± 32 |
| +15.0 $\mu$l OHC X | 643 ± 33 |
| +30.0 $\mu$l OHC X | 783 ± 79 |
| 2% FCS | 1051 ± 23 |
| +15 $\mu$l PBS | 1127 ± 51 |
| +7.5 $\mu$l OHC X | 1059 ± 38 |
| +15.0 $\mu$l OHC X | 920 ± 35 |
| +30.0 $\mu$l OHC X | 1140 ± 57 |

It can be seen from the results summarized in Table V that rat skin fibroblasts cannot be stimulated by OHC X.

If the test results summarized in Table IV are compared with the test results summarized in Table V it becomes evident that the observed mitogenic activity of OHC X is specific to osteoblasts.

EXAMPLE 8

Measurement of the Biological Activity of Irradiated OHC

OHC prepared as in Examples 1 or 2 is irradiated with 25 kGy (2.5 Mrad). The experiment is performed as in Example 3. The results are shown in FIG. 8.

Figure 8:
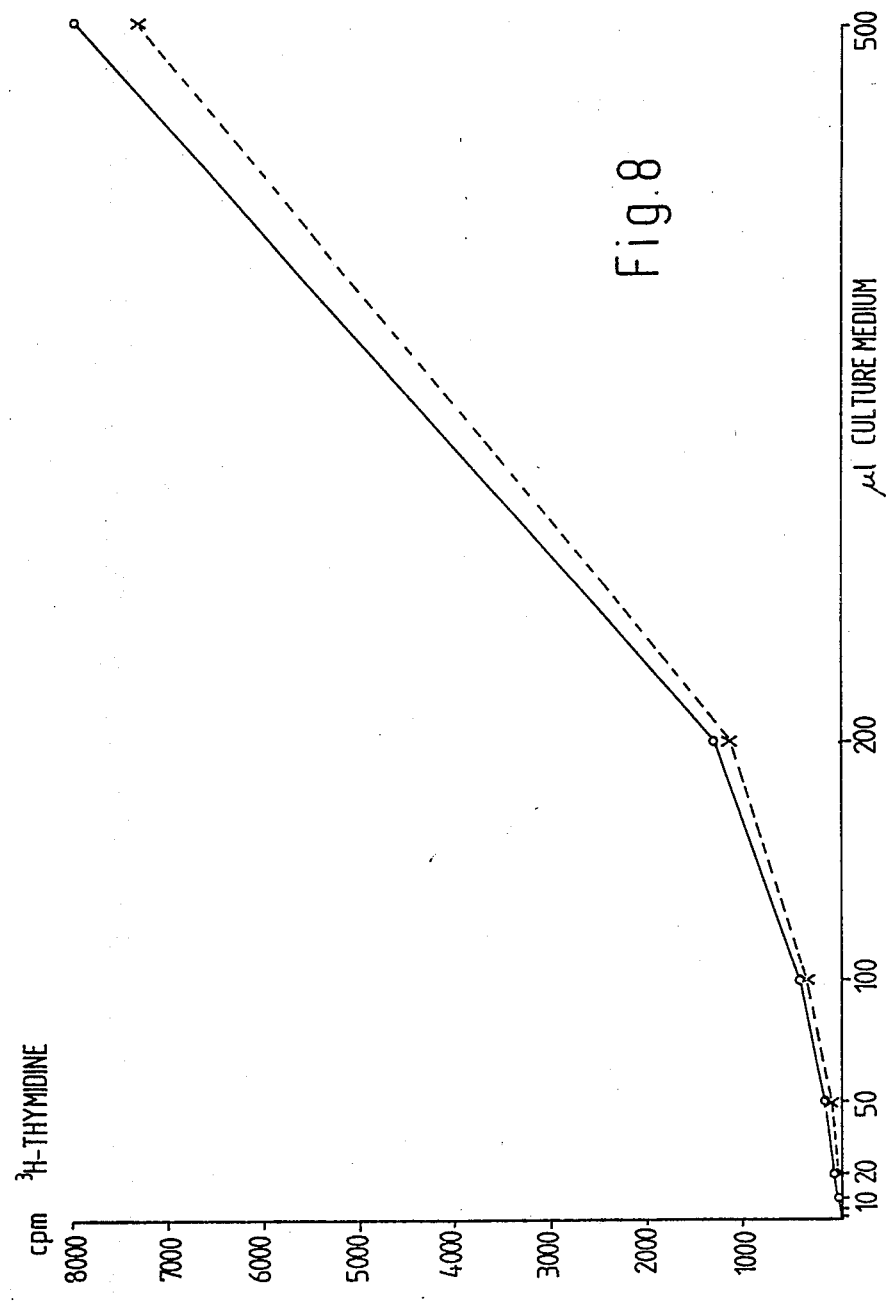
FIG. 8 shows stimulation of $^3$H-thymidine uptake in 3T3 fibroblasts with irradiated and nonirradiated OHC extract. The irradiated OHC extract exhibits a protein content of 690 $\mu$g/ml (_). The nonirradiated OHC extract exhibits a protein content of 670 $\mu$g/ml (—). The abscissa gives the concentration of OHC extract in $\mu$l/2.5 ml culture medium. The ordinate shows the uptake of $^3$H-thymidine in cpm.

FIG. 8 summarizes the results from $^3$H-thymidine incorporation by 3T3 fibroblasts for stimulation using various amounts of a PBS extract of irradiated and nonirradiated OHC. It can be seen from FIG. 8 that irradiation does not affect the biological activity of OHC.

EXAMPLE 9

Comparison of the Effect of OHC with the Effect of Known Preparations for the Same Area of Indication 1 g of each of the substances being assayed is weighed out into a screw top vial and 10 ml of PBS are added. After 2 hrs of shaking at room temperature, centrifugation for 10 minutes at 3600 r.p.m. in an MSE table centrifuge follows. The clear supernatants are decanted and the precipitates discarded. The protein content of the solutions is measured as described by Bradford (Anal. Biochem. 72 (1976), p. 248). Uptake of $^3$H-thymidine in 3T3 fibroblasts is stimulated as in Example 3 and evaluated.

Table VI summarizes the preparations that were compared and their extractable protein content.

TABLE VI

| | Amount of extractable protein/ml solution |
|---|---|
| Lencoll ® | 330 μg |
| Lenphos ® | 105 μg |
| Lensol ® | 3850 μg |
| Lensol ® agglomerated | 4200 μg |
| Osspulvit ® | 24 μg |
| Mitsubishi Cookies ® | 82 μg |
| PMC ® | 400 μg |
| Osteotrophic Concentrate | 22 μg |
| Canzocal ® | 28.5 μg |
| OHC (Invention) | 600 μg |

Figure 9:
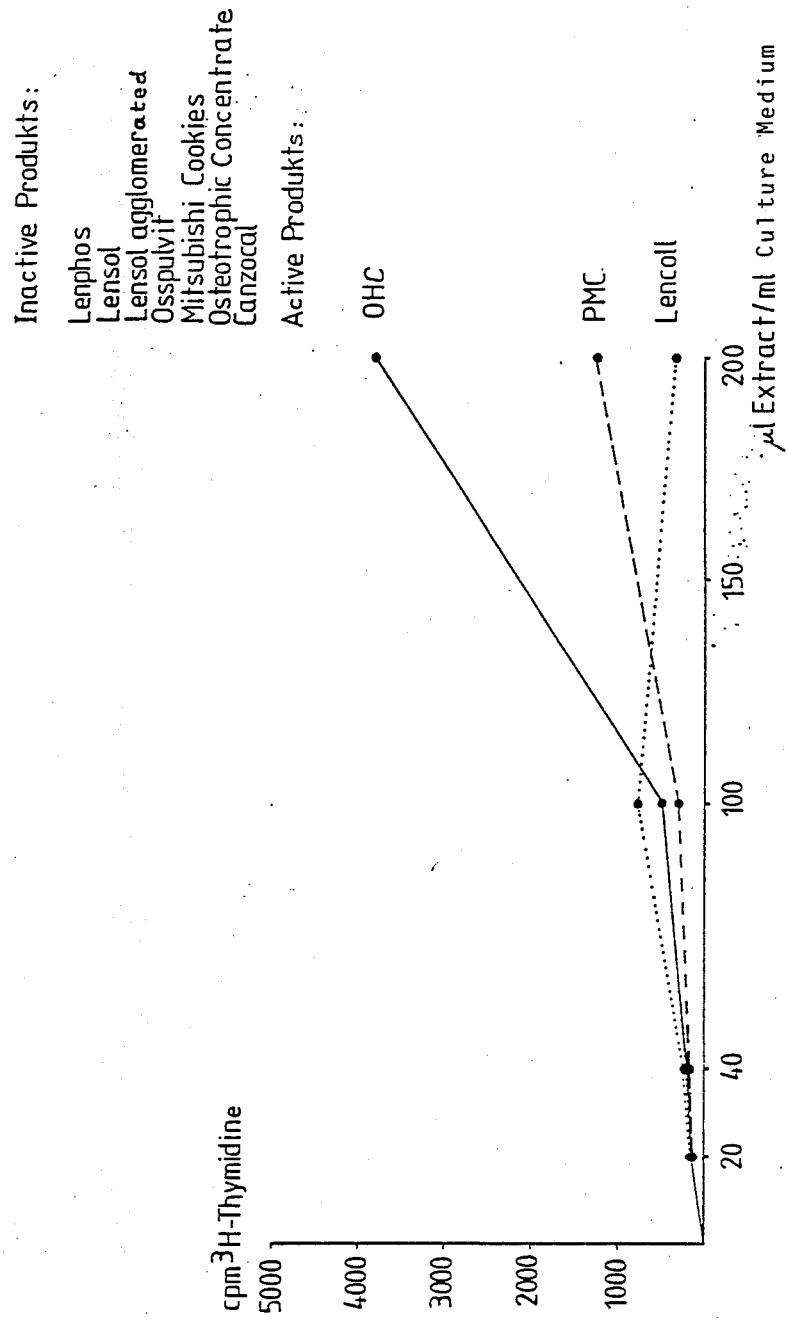
FIG. 9 shows stimulation of $^3$H-thymidine uptake on 3T3 fibroblasts by Lencoll®, Lenphos®, Lensol®, Lensol agglomerated, Oss Pulvit, Mitsubishi Cookies, osteotrophic concentrate, Canzocal, PMC and OHC. The abscissa gives the concentration in the sample tested in $\mu$l/ml culture medium; the ordinate shows $^3$H-thymidine uptake in cpm.

The experimental results are summarized in FIG. 9. Inactive substances are not distinguishable from the blank and hence cannot be depicted.

It can be seen from FIG. 9 that OHC is markedly superior to the other products in stimulating DNA synthesis.

EXAMPLE 10

The Effect of OHC on Bone Healing in Animal Experiments

The effect of OHC on bone healing is ascertained in a study using 60 adult rabbits. Precision engineering is used to introduce cartilage/bone defects identical in size and location in the distal femoral epiphysis of both knee joints.

The animals are distributed at random into four groups of 15 animals each. An untreated group acts as the control. A first group receives 830 mg of OHC (178.0 mg calcium) daily, the second group receives 510 mg of ashed OHC (i.e. bone mineral without active, organic ingredients; 178.9 mg calcium) daily and a third group receives 650 mg of calcium carbonate daily (189.7 mg calcium). Table VII details the experimental design.

TABLE VII

| | Experimental Design | | | |
|---|---|---|---|---|
| Test group | Postoperative duration of experiment | Number of test animals | Daily dose per animal, administered orally | Additional Ca amount in the daily dose in mg |
| Control group | 35 | 5 | — | — |
| | 56 | 5 | | |
| | 84 | 5 | | |
| OHC group | 35 | 5 | 1 tablet @ 830 mg | 178.0 |
| | 56 | 5 | | |
| | 84 | 5 | | |
| OHC (ashed) | 35 | 5 | 1 tablet @ 510 mg | 178.9 |
| | 56 | 5 | | |
| | 84 | 5 | | |
| CaCO$_3$ (Os-Cal) | 35 | 5 | 1 tablet @ 650 mg | 189.7 |
| | 56 | 5 | | |
| | 84 | 5 | | |

From day 7 to day 23 after introduction of the defects the animals are treated with a series of fluorescence markers. 5 animals are sacrificed after 5,8 and 12 weeks respectively. The histological sections are examined with a fluorescence microscope with standardized localisation and definition of the sectional plane in the region of the bone defect. The microphotographs are evaluated on an index point system based on fluorescence intensity, nature and degree of defect filling, and structure of the new bone growth. Table VIII lists the results.

TABLE VIII

| | Averages and Standard Deviations of Summated Index Points according to Differing Treatment and Test Duration | | |
|---|---|---|---|
| Groups | 35 days | 56 days | 84 days |
| Control | 17.8 ± 3.6 | 22.0 ± 8.5 | 16.2 ± 2.8 |
| OHC | 24.3 ± 4.8 | 31.8 ± 1.1 | 34.3 ± 2.4 |
| OHC (ashed) | 24.4 ± 4.2 | 28.2 ± 4.1 | 25.0 ± 12.8 |
| CaCO$_3$ (Os-Cal) | 20.0 ± 7.1 | 27.2 ± 6.3 | 29.0 ± 6.1 |

The three treated groups show significantly improved mineralization over the untreated control group. In contrast to the two other active treatments therapy with OHC results in marked improvements in the healing of bone defects.

The comparison of the test results obtained with OHC and with ashed OHC makes it clear that if the organic components are destroyed the advantageous effect of OHC is lost.

EXAMPLE 11

The Effect of OHC on the Ultrastructure of the Articular Chondrocyte in Animal Experiments The effect of OHC on the articular chondrocyte ultrastructure after corticoid damage is investigated in a series of in vivo tests with rats. A quantitative assessment is made possible by the use of a new, reproducible morphometric method; see M. Annefeld, Int. J. Tiss. Reac., Vol. VII [4], (1958), pp. 273–289.

The experiments are carried out with three groups of 5 male Wistar rats. The first group is a control group and is not treated. Dexamethasone is administered to the second group intramuscularly, and the third group is given dexamethasone intramuscularly and, in addition, OHC orally. The experimental design is summarized in Table IX.

TABLE IX

| Group | Dosage per animal and week | Total number of drug doses given | Duration of the investigation in weeks | Number of animals |
|---|---|---|---|---|
| Control | — | — | 5 | 5 |
| Dexamethasone | 2 × 0.5 mg i.m. | 10 | 5 | 5 |
| Dexamethasone/OHC | 2 × 0.5 mg i.m.<br>5 × 50 mg p.o. | 10<br>25 | 5<br>5 | 5<br>5 | i.m. = intramuscularly;
p.o. = orally

After they have been treated for five weeks the animals are sacrificed. All the cartilage tissue from the femur and tibia of both knee joints is excised, and the tissue is prepared for electron microscopy. 50 chondrocytes from each animal are analyzed morphometrically.

Compared to the controls, the animals treated with dexamethasone show a reduction in the length of the endoplasmic reticulum and in the overall surface of the Golgi apparatuses of their articular chondrocytes, along with increased chondrocyte mortality. These electron microscope findings are clear proof of damage to the articular chondrocytes by corticosteroids.

The animals that were in addition treated with OHC reveal a much smaller reduction of the endoplasmic reticulum and of the surface of the Golgi apparatuses in their articular chondrocytes. OHC lowers the mortality rate of the chondrocytes, which dexamethasone had increased, to below even the control level, and at the same time OHC also increases the overall surface and the number of mitochondria. These findings point to the fact that after oral administration OHC increases the metabolism of the chondrocytes. Table X gives a summary of the test results.

TABLE X

Morphometric determination of chondrocyte ultrastructure after tests lasting 5 weeks

| | Control | Dexamethasone | Dexamethasone OHC |
|---|---|---|---|
| endoplasmic reticulum, total length, μm | 28.2 | 1  21.6 | —  23.6  — |
| Golgi apparatuses, overall surface (μm$^2$) | 2.58 | 1  2.12 | —  2.71  2 |
| Mitochondrial number, overall surface (μm$^2$) | 13.1<br>1.28 | 1  16.1<br>—  1.35 | 1  20.4  2<br>1  1.96  2 |
| Cell mortality, % | 2.17 | 4.00 | 1.25 |

Influence of dexamethasone and OHC:
1 = statistically significant difference between the control and test groups
2 = statistically significant difference between groups treated with dexamethasone and those given both dexamethasone and therapy
p = 0.01,
n = 250 per group.

It can be seen from this test that the results obtained in cytobiological tests with OHC in vitro (see Examples 3 through 6) also retain their validity in vivo. Furthermore, the results show that OHC prevents the known negative effects of corticosteroids on cartilage and bone cells by regulating the cell metabolism.

EXAMPLE 12

Use of OHC to Support Bone Healing

The influence of OHC in bone fracture healing versus a placebo is clinically investigated in a double blind study.

After randomization 85 cases of tibia shaft fractures are treated for six weeks with one of the two medications. Table XI provides an overview of the age of the patients and type of treatment.

TABLE XI

| | Number of Patients | |
|---|---|---|
| | Placebo | 1'400 mg OHC/d |
| >55 years | 13 | 13 |
| <55 years | 36 | 23 |
| | 49 | 36 |

The consolidation of the tibia shaft fractures is determined in accordance with the following parameters:
(a) immobility at the fracture site
(b) freedom from pain
(c) mobility of the broken extremity
(d) maximum loading of the broken extremity
(e) radiological findings.

In the case of older patients consolidation by treatment with OHC occurs after approximately 11 weeks, that is to say markedly more rapidly than when the placebo is employed (14.2 weeks, $p<0.05$). In the case of the younger patients the difference is without statistical significance (12.5 weeks versus 11.5 weeks). It is evident from these test results, once it is remembered that in the case of the placebo group the number of complications in healing requiring surgery is three times higher, that OHC promotes ordered fracture healing.

EXAMPLE 13

Treatment of Osteoporosis with OHC

In a controlled study the influence of OHC on corticoidinduced osteoporosis is investigated.

64 patients at least 50 years old who have been receiving corticosteroids for treating rheumatic arthritis are randomised to statistically identical groups for treatment. The patients in group 1 receive 4.9 g of OHC daily in addition to their usual treatment. No OHC is administered to the patients of Group 2.

At the end of the treatment period the loss in stem height and reduction in radius bone density is markedly lower in the group treated with OHC than in the control group. Other parameters such as ulnar bone density and back pains are likewise greatly improved in the group treated with OHC as against the controls, but do not attain statistical significance. The results are summarized in Table XII.

TABLE XII

Differences in Osteopenia Indices after 1 Year of Supplemental OHC Therapy

| | Controls | OHC | p values |
|---|---|---|---|
| Mean loss of stem height in cm ± S.D. | 1.16 = 0.71 | 0.87 = 0.58 | 0.01 < p < 0.05 |
| Mean loss of radial bone density BMC/W ± S.D. | 0.056 = 0.035 | 0.043 = 0.029 | p < 0.05 |
| Mean loss of ulnar bone density BMC/W ± S.D. | 0.033 = 0.031 | 0.030 = 0.026 | n.s. |
| Number of new vertebral crush fractures on radiographs | 4 | 3 | n.s. | n.s. = not significant

Treatment with OHC is also successful in preventing progression of osteopenia in rheumatics treated with steroids. It is evident from the study that OHC treatment should commence as soon as systemic corticosteroid treatment begins, without waiting for the clinical symptoms evincing the development of osteopenia.

EXAMPLE 14

Treatment of Osteoporosis with OHC versus Calcium

In a clinical study the effect of vitamin $D_2$, of OHC and of calcium gluconate as part of the therapy for primary cirrhosis of the liver is investigated, the latter condition resulting in rapid bone loss.

Vitamin $D_2$ is administered parenterally to 65 postmenopausal women with osteoporotic changes in primary liver cirrhosis. This collective of patients is divided into three groups on a statistical basis. The first group comprises 22 patients and receives only vitamin $D_2$ (control). The 21 patients forming the second group receive 6.6 g of OHC daily over and above their vitamin $D_2$ therapy. The third group of 22 patients receive calcium in a dose equivalent to that of the OHC given to the patients of the second group, i.e. 4 effervescing tablets of calcium gluconate per day.

After 14 months of therapy it is established that the parenteral therapy with vitamin $D_2$ is not sufficient on its own to arrest the bone loss which was measured by means of the metacarpal index, that, furthermore, the combination of vitamin $D_2$ and calcium gluconate has only barely sufficed to halt further bone loss, and that only the combination of vitamin $D_2$ with OHC produced a statistically significant 11.6% gain in the bone cortex as compared with the control. The experimental results are summarized in FIG. 10.

These test results show that OHC is not merely a pure calcium preparation.

EXAMPLE 15

Treatment of Osteoporosis with OHC 36 patients who have been under treatment with prednisolone and azathioprin for at least one year for chronically active autoimmune hepatitis are divided into two groups on a statistical basis. The 18 patients in the first group receive 6.6 g of OHC daily for two years, while the 18 patients in the control group receive no OHC.

The test results are obtained by photodensitometry and with the help of bone biopsies. After two years the control group has suffered a statistically significant reduction in the mineral content of the radius BMC ("single" photodensitometry) and in the cortex thickness of the iliac crest CPT (bone biopsy) (see FIGS. 11 and 12). It is found at the bone biopsy that in the control group there has been a distinct reduction in trabecular bone volume (TBV) (see FIG. 12). In the case of OHC therapy, on the other hand, the mineral content of the radius remains constant (see FIG. 11), trabecular bone volume increases and the reduction in cortex thickness is statistically significantly less than in the control group (FIG. 12). During the two year period of treatment three patients from the control group exhibit vertebral deformations, but not a single patient from the OHC group. Five patients exhibit a trabecular bone volume (TBV) below the "vertebral fracture threshold" postulated by Meunier of 11%±3%, yet none of the four patients at risk who were treated with OHC develops vertebral fracture. However, three of the control patients (TBV>16%) exhibit vertebral deformations, with accompanying falls in TBV levels below 11%.

EXAMPLE 16

The Effect of OHC following Oophorectomy

In a retrospectively controlled study conventional bone specific parameters (the bone specific isoenzyme of alkaline phosphatase - osteoblast marker; hydroxyproline in the urine - osteoclast marker; "tartrate resistent" acidic phosphatase - osteoclast marker) are used to show that on the one hand enzyme levels in the serum rise sharply immediately after oophorectomy (a sign of high and intensive bone turnover), and on the other hand therapy with 7.5 g of OHC daily for 9 months normalizes the increased bone turnover levels and thereby lowers the risk. Parallel to the biochemical findings, bone gain is found when OHC is administered, and this can be measured via the metacarpal index. The cortical bone loss of 1.1±0.6% per annum which was measured prior to therapy changes in the case of OHC therapy to a statistially significant positive bone gain of 0.2±0.3% per annum.

EXAMPLE 17

Computer Tomographic Measurement of the Effect of OHC in Manifest Osteoporosis 11 osteoporotic patients (2 men, 9 women) are treated for two years with 7.5 g of OHC daily and examined using quantitative computer tomography; see P. Rueg-segger et al., J. Comput. Assist. Tomogr. 5 (1981), pp. 384–390. Based on the age structure of the patients, on average a spongiosa density loss of 2.7% per annum would be expected.

However, in the case of OHC therapy virtually all the patients treated are found to exhibit a small increase in the spongy bone mass. Such an increase has otherwise only been observed in the case of sodium floride therapy, but in the latter case the effect was not so regular and continuous and found only in some patients (responders). Latest results, see M. A. Dambacher et al. Bone 7, 199–205 (1986) show that the standard therapy in osteoporosis (sodium fluoride or combination of sodium fluoride and calcium) cannot arrest the progression of the disease (bone loss cannot be completely inhibited; vertebral crush fracture rate increased). Spontaneous trabecular bone gain in untreated patients has so far never been observed.

What is claimed is:

1. A method for producing an ossein hydroxyapatite compound comprising the steps of:
    (a) crushing the bones of a mammal aged from prenatal to approximately 12 months old to produce bone particles of about 1 cm in size;
    (b) acidifying said bone particles of step (a) to pH 5.0 to 5.5 with an acid;
    (c) dehydrating and degreasing said acidified bone particles with a hydrophilic and lipophilic solvent to a residual water and residual fat content of about 5%;
    (d) drying said dehydrated and degreased bone particles at reduced pressure at 20° to 80° C. to a solvent content of about 1%;
    (e) pulverizing said bone particles to a particle size of about 50 to 300 micrometers; and
    (f) sterilizing said bone particles such that an ossein hydroxyapatite compound is produced,
    wherein said compound has the following dry substance analytical characteristics:

| | |
|---|---|
| Organoleptic Test | Fine to slightly granular, beige-gray powder with faint natural odor |
| Identity | Calcium and phosphatase identified<br>Collagen identified |
| Water Content | <7% |
| Total ash | 51.3–62.7% |
| Calcium | 19.2–23.6% |
| Phosphorus | 8.9–10.9% |
| Collagen | 23.4–28.6% |
| Non-collagenic Proteins/Peptides | 7.2–10.8% |
| Trace Elements | F, Na, K, Mg, Fe, Zn, Cu and Ni identified |
| Phosphatase Activity | 0.5–15 mE/mg |
| Anomalous Toxicity | No signs of intolerance |
| Total Microbial Content | $<10^4$/g |
| Yeasts | $<10^2$/g |
| Enterobacteriaceae | $<10^2$/g |
| Specific Microbe Species | Absent/g | and said compound is characterized by the following biological activities:

(i) stimulation of DNA synthesis in osteoblasts, chondrocytes, and fibroblasts, (ii) stimulation of protein synthesis in chondrocytes and fibroblasts, (iii) selective stimulation in chondrocytes of collagen synthesis, as a fraction of total protein synthesis, (iv) induction of the synthesis of proteins x and y in chondrocytes, and (v) promotion of differentiation of non-specific mesenchymal cells to chondrocytes or osteoblasts.

2. The method of claim 1 further comprising, after step (a), drying said bone particles at reduced pressure at about 20° to 80° C. to a residual water content of about 10 to 25%.

3. The method of claim 1 wherein step (c) of the method comprises dehydrating with a hydrophilic solvent at 20° to 80° C. to a residual water content of about 5% and then degreasing with a lipophilic solvent at 20° to 80° C. to a residual fat content of about 5%.

4. The method of any of claims 1–3, wherein said bones are long bones.

5. The method of any of claims 1–3, wherein said bones are long bones of bovines.

* * * * *